US00PP08592P

United States Patent [19]

Kordes

[11] Patent Number: Plant 8,592

[45] Date of Patent: Feb. 15, 1994

[54] ROSE PLANT KORBIRAC

[75] Inventor: Wilhelm Kordes, Sparrieshoop, Fed. Rep. of Germany

[73] Assignee: Bear Creek Gardens, Inc., Medford, Oreg.

[21] Appl. No.: 963,914

[22] Filed: Oct. 19, 1992

[51] Int. Cl.[5] ..... A01H 5/00

[52] U.S. Cl. ..... Plt./11

[58] Field of Search ..... Plt. 11, 16, 25, 15

*Primary Examiner*—Howard J. Locker
*Assistant Examiner*—Erich E. Veitenheimer
*Attorney, Agent, or Firm*—Klarquist, Sparkman, Campbell, Leigh and Whinston

[57] ABSTRACT

Grandiflora rose plant having distinctive vigorous upright growth habit, flower clusters with stems long enough to cut, thick leathery petals, a unique light orange with light yellow reverse flower color and a long flower life both on the plant and in the vase.

1 Drawing Sheet

The present invention relates to a new and distinct variety of rose plant of the grandiflora class which was originated by me by crossing the variety MerKor, U.S. Plant Pat. No. 3,724, with an unnamed seedling.

The primary objective of this breeding was to produce a new rose variety which is vigorous and healthy with many blooms in an appealing color. The objective was substantially achieved along with other desirable improvements as evidenced by the following unique combination of characteristics which are outstanding in the new variety and which distinguish it from its parents, as well as from all other varieties of which I am aware:

1. Thick, leathery petals;
2. Long flower life both on the plant and in the vase;
3. Unique flower color;
4. Vigorous, very upright growth habit;
5. Flower presentation often in clusters that have long individual stems.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—MerKor, U.S. Plant Pat. No. 3,724.

*Pollen parent.*—Unnamed seedling.

Classification:

*Botanical.*—*Rosa hybrida.*

*Commercial.*—Grandiflora.

FLOWER

Observations made from specimens grown in a garden in Somis, Calif. from March to August, 1992.

Blooming habit: Recurrent.

Bud:

*Size.*—1¼ inches long when the petals start to unfurl.

*Form.*—Long, pointed ovoid.

*Color.*—When sepals first divide, bud color is Orange Red Group 32C on areas of the bud mixed with Yellow Orange Group 21D on other areas of the bud. When half blown, the upper sides of the petals are Orange Red Group 32B on the petal edges changing to Orange Group 24C over most of the petal surface; and the lower sides of the petals are Yellow Orange Group 22D with some Orange Group 29B near the top edge of the petal.

*Sepals.*—Color: Green Group 138B. Surface Texture: Covered in fine hairs. There are three normally appendaged sepals. There are two unappendaged sepals with hairy edges.

*Receptacle.*—Color: Green Group 138C. Shape: Funnel. Size: Large (⅜×⅜ inches). Surface: Hairy.

*Peduncle.*—Length: Short (1½ inch). Surface: Glandular. Color: Medium green and bronzy. Strength: Stiff, erect.

Bloom:

*Size.*—Medium. Average open size is 4 inches in diameter and 1¼ inches in depth.

*Borne.*—Singly, several together, in clusters from 3 to 7 blooms. If in clusters: Rounded.

*Stems of flowers in cluster.*—Medium, strong (12 to 14 inches).

*Form.*—When first open: High centered. Permanence: Retains its form to the end; outer petals curl back.

*Petalage.*—Number of petals under normal conditions: 30.

*Color.*—The upper side of the petals is Mainly Orange Group 24C changing to Orange Red Group 32B on the petal edges. The reverse side of the petals is Yellow Orange Group 22B with some Orange Group 29B near the top edge of the petal. The color of the base of petals intensifies to Bright yellow half moon at the point of attachment (¼×¼ inches) Yellow Orange Group 15B at the petal base. The major color on the upper side is Orange Group 24C.

*Variegations.*—Occasional green streak on the guard petals.

*Discoloration.*—The general tonality at the end of the first day: No change. At the end of the third day: Some color change on the petal edges. Gradual increase in Orange-Red Group 32B on the petal margins.

*Fragrance.*—Slight.

Petals:

*Texture.*—Thick, leathery.

*Shape.*—Round.

*Form.*—Tips slightly recurved, edges slightly quilled.

*Arrangement.*—Imbricated, with few petaloids in the center.

*Persistence.*—Hang on and dry.

*Lastingness.*—On the plant: Long (7 days). As a cut flower: Long (8 to 9 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Reddish near the stigma — otherwise white.

*Stigmas.*—Color: Greenish white.

Form: Bush.

Growth: Very vigorous. A mature plant in Somis, Calif., is about 6 feet in height and 4 feet in width.

Foliage:

*Number of leaflets on normal mid-stem leaves.*—5 or 7.

*Size.*—Medium (4½ to 5×3 to 3½ inches).

*Quantity.*—Abundant.

*Color.*—New foliage: Gray-Purple Group 183A. Old foliage: Green Group 139A.

Leaflets:

*Shape.*—Pointed oval.

*Texture.*—Upper side: Leathery.

*Edge.*—Serrated.

*Serration.*—Single, small.

*Petiole rachis.*—Color: Green.

*Petiole underside.*—Rough with prickles.

*Stipules.*—Medium, bearded.

*Disease resistance.*—Susceptible to mildew, but resistant to rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium.

*Color when young.*—Red.

Small prickles:

*Quantity.*—On main stalks: Few. On laterals: Few.

I claim:

1. A new and distinct variety of rose plant of the grandiflora class, substantially as herein shown and described, characterized particularly as to novelty by the unique combination of its vigorous upright growth habit, flower clusters with stems long enough to cut, thick leathery petals, a unique light orange with light yellow reverse flower color and a long flower life both on the plant and in the vase.

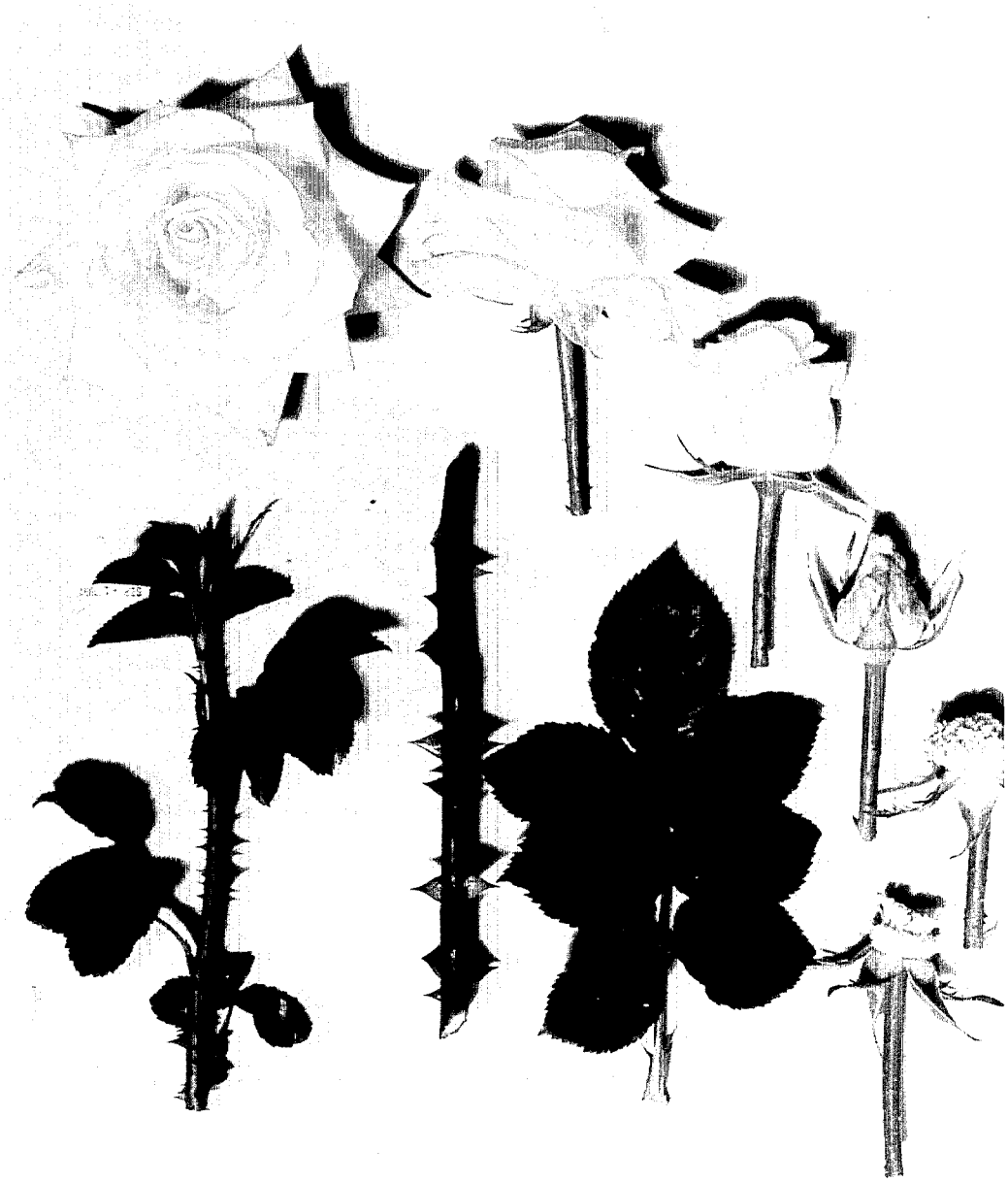

* * * * *